United States Patent
Bonnema

[11] Patent Number: 5,944,508
[45] Date of Patent: Aug. 31, 1999

[54] PORTABLE HEATED APPLIANCE WITH CATALYTIC HEATER WITH IMPROVED IGNITION SYSTEM

[75] Inventor: James V. Bonnema, Essex County, Mass.

[73] Assignee: The Schawbel Corporation, Boston, Mass.

[21] Appl. No.: 08/834,727

[22] Filed: Apr. 1, 1997

[51] Int. Cl.⁶ ............................. F23D 3/40; F23D 14/18
[52] U.S. Cl. ..................... 431/255; 431/326; 431/329; 126/408; 126/409
[58] Field of Search ................... 431/326, 268, 431/255, 328, 329, 7; 126/403, 404, 406, 408, 409

[56] References Cited

U.S. PATENT DOCUMENTS

| | | | |
|---|---|---|---|
| 3,975,140 | 8/1976 | Placek | 431/329 |
| 4,243,017 | 1/1981 | Diederich . | |
| 4,248,208 | 2/1981 | Diederich . | |
| 4,361,133 | 11/1982 | Bonnema . | |
| 4,374,528 | 2/1983 | Tittert . | |
| 4,378,783 | 4/1983 | Hunter | 431/329 |
| 4,382,448 | 5/1983 | Tittert . | |
| 4,699,123 | 10/1987 | Zaborowski . | |
| 5,123,837 | 6/1992 | Farnham et al. | 431/258 |
| 5,320,089 | 6/1994 | Schaefer et al. . | |
| 5,394,862 | 3/1995 | Firatli et al. . | |
| 5,485,829 | 1/1996 | Santhouse et al. | 431/255 |

FOREIGN PATENT DOCUMENTS

| | | | |
|---|---|---|---|
| 2271513 | 12/1975 | France | 431/329 |
| 0000716 | 1/1987 | Japan | 431/268 |
| 62-716 | 1/1987 | Japan . | |

*Primary Examiner*—Carl D. Price
*Attorney, Agent, or Firm*—Levisohn, Lerner, Berger Langsam

[57] ABSTRACT

A portable catalytically heatable appliance is provided. The appliance includes a catalyst support structure to flamelessly combust liquid or gaseous fuel and thereby provide a lower temperature heat source than a heat source that combusts fuel via flame. The fuel is ignited inside the catalytic support structure by a spark electrode. The ignition of the fuel inside the structure obviates the need for separate flame arresters. The ignition system includes a piezoelectric device that causes a voltage potential to form between the electrode and the catalytic support structure. A spark jumps from the electrode to an interior surface of the structure and ignites the fuel inside the structure, causing a flame to propagate. The flame heats the catalytic structure to an activation temperature, after which the fuel is combusted flamelessly on the surface of the catalytic structure.

44 Claims, 5 Drawing Sheets

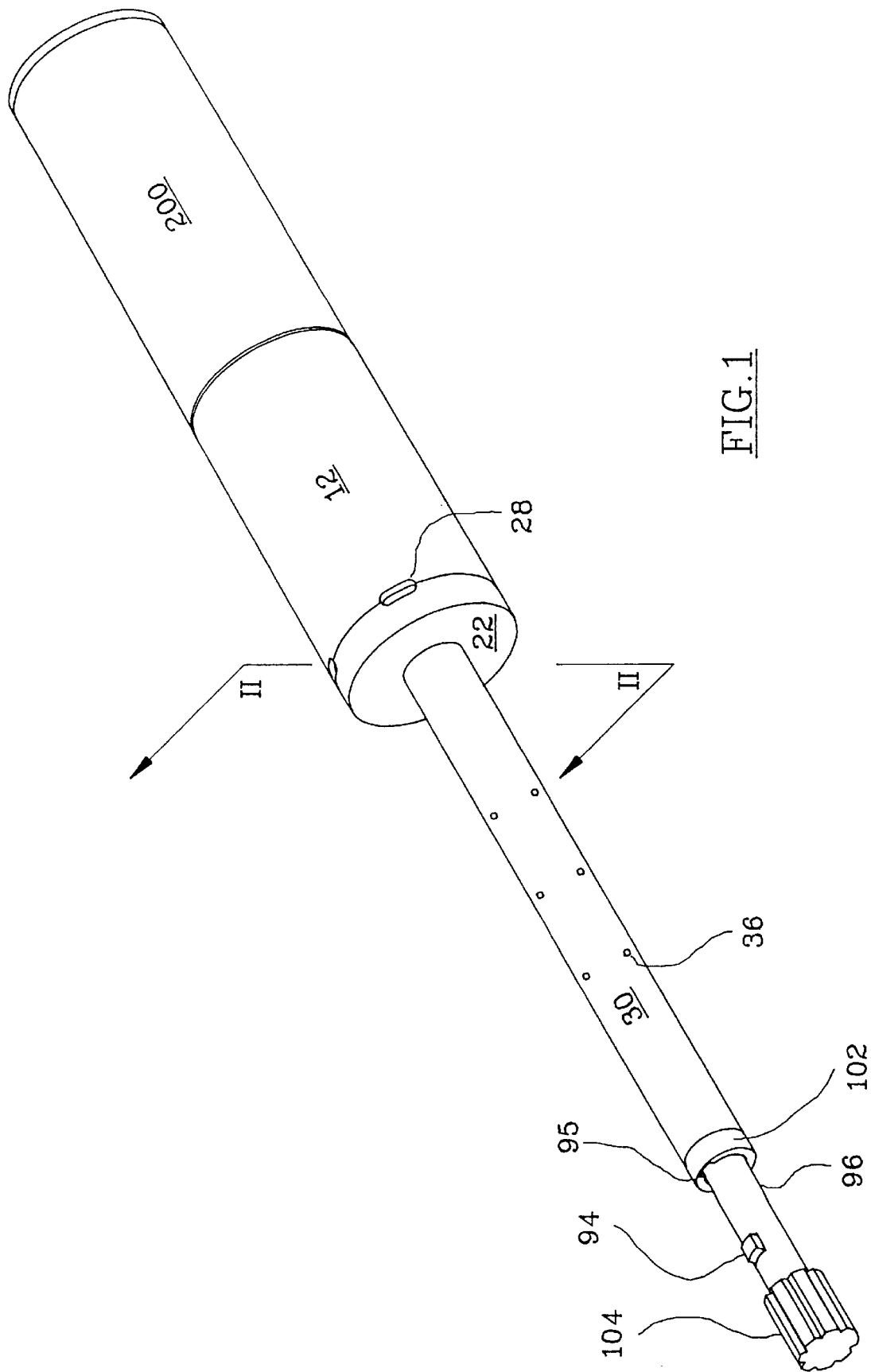

PORTABLE HEATED APPLIANCE WITH CATALYTIC HEATER WITH IMPROVED IGNITION SYSTEM

BACKGROUND OF THE INVENTION

1. Field of the Invention

This invention relates to liquid- or gas-fueled heatable appliances, and more specifically to a portable heated appliance having a catalytic heater.

2. Description of the Related Art

Devices enabling flameless combustion of fuels such as butane or propane are known. One such device is described in U.S. Pat. No. 4,361,133 to Bonnema, the inventor of the present invention. This conventional device includes catalytically-coated quartz wool arranged between two spiral support springs. The quartz wool enables the flameless combustion of a fuel/air mixture and can be utilized in a personal appliance requiring a heat source, such as a curling iron. The catalytic combustion of the fuel/air mixture only occurs when the catalytically active material is heated to a certain activation temperature. An activation device provides the necessary energy to raise the catalyst to the required temperature. The activation device ignites, via a spark or external flame, a fuel/air mixture entering the combustion chamber of the appliance. The flame is extinguished fairly quickly, however the ensuing energy released from the ignition is sufficient to heat the catalytically active material to the activation temperature. Subsequently, flameless combustion of the fuel/air mixture takes place.

This design has suffered from several drawbacks. First, the quartz wool carrier itself is mechanically unstable, and must be fixed carefully to its support springs. Further, fibers from the quartz wool can fall off of the main structure and clog the fuel metering nozzle or other portions of the fuel flow path; this loss of fiber also may result in a reduction of catalytic activity of the quartz wool, since some of the catalytically active material is being lost. Also, the quartz wool does not necessarily heat evenly, resulting in hot spots. Finally, since this device is used in the hair care art, it is subject to many hair care products, e.g., shampoo, hair spray, etc., which are prevalent in the ambient air. These hair care products, particularly those containing silicone, have an adverse effect on the useful life of the catalyst, usually resulting in an unacceptably high amount of energy required to cause flameless combustion.

Another conventional device has been described in U.S. Pat. No. 5,320,089 to Schaefer et al. In this device, instead of quartz wool, an expanded metal foil structure (approximately 0.001 inches thick) is used as the carrier structure for the catalytically active material. A fuel/air mixture is supplied as before, and a spark is applied outside the carrier structure to cause an explosion which heats the catalyst to activation temperature. A subsequent design described in U.S. Pat. No. 5,394,862 to Firalti et al. adds a starter catalyst consisting of a wire or wires attached to the outside of the metal carrier structure to facilitate achievement of the activation temperature.

The Schaefer et al. and Firalti et al. patents describe a metal catalytic substrate that is more rugged than the quartz fiber structure used in the Bonnema patent, yet it is required to have a very low mass and high surface area such that a single explosion of the volume of gas in a container around the catalyst will sufficiently raise its temperature to the point where the catalytic combustion will begin. There remain several disadvantages to this construction. First, the metal substrate described is still a rather delicate structure which would not be easy to manufacture and would be susceptible to damage or misalignment by jostling the appliance. Second, if the catalyst should lose activity, for example, from contamination by hair care products, to the point where the heat of a single explosion will no longer initiate catalytic reaction, then it is impossible to use the appliance. Multiple explosions would not be effective, since the fuel/air mixture must be replenished and be allowed to build up in the combustion chamber between explosions, during which time the catalyst will have cooled. Moreover, the explosion used for ignition takes place outside the tubular catalyst structure. In order to manufacture a safe appliance, a flame arrester must be placed between the exploding volume of the fuel/air mixture and the outside environment. Flame arresters are especially important for heated hair care appliances, because many hair care products are highly flammable.

In light of the above deficiencies of conventional devices, there is a need in the art for a catalytic heating system that is durable, will reliably ignite, is simple to manufacture, and does not require additional flame arresters.

SUMMARY OF THE INVENTION

Accordingly, it is an object of this invention to provide a portable catalytic heating system that will reliably ignite even after extended use.

It is another object of the invention to provide a portable catalytic heating system that is mechanically durable and less fragile than conventional systems.

It is yet another object of the invention to provide a portable catalytic heating system that possesses inherent flame arresting features and does not require additional structures or devices to prevent the propagation of flames outside the device.

It is still another object of the invention to provide a portable catalytic heating system that is easy to manufacture.

The above and other objects are achieved by the present invention. One embodiment of the invention includes a catalyst assembly for a portable heating appliance that possesses an enclosed structure having an opening at one end adapted to receive fuel. An ignition source is mounted on one of the ends of the structure and extends into the interior of the structure. A burner nozzle is disposed inside the structure, and catalytically active material is provided on a surface of the structure. Preferably, the catalytic structure is substantially tube-shaped, and the burner nozzle is preferably a wire mesh screen. The ignition source is preferably a spark electrode.

A second embodiment of the invention includes a portable heating appliance that possesses a housing containing a flow path for fuel and a catalyst assembly disposed in communication with the fuel flow path. The catalyst assembly includes an enclosed structure having an opening at one end adapted to receive fuel exiting from the flow path. An ignition source, preferably a spark electrode, is mounted on one of the ends of the structure and extends into the interior of the structure. A burner nozzle, preferably a screen, is disposed inside the structure, and catalytically active material is provided on a surface of the structure, preferably an interior surface.

A third embodiment of the invention includes a portable heating appliance possessing a housing containing a flow path for fuel and a substantially tube-like barrel projecting from the housing preferably in a cantilever fashion, the interior of which is in communication with the fuel flow path. A piezoelectric ignitor is disposed in the free end of the barrel and is adapted to ignite fuel inside the barrel. The piezoelectric ignitor further includes a spark electrode and a non-conductive mounting plug both disposed in the interior of the barrel. One end of the spark electrode is disposed in the mounting plug so that the spark electrode is exposed at an end of an inner portion of the mounting plug.

BRIEF DESCRIPTION OF THE DRAWINGS

FIG. 1 is a perspective view of a curling iron according to the invention.

DETAILED DESCRIPTION OF THE PREFERRED EMBODIMENTS AND DRAWINGS

Figure 2A:
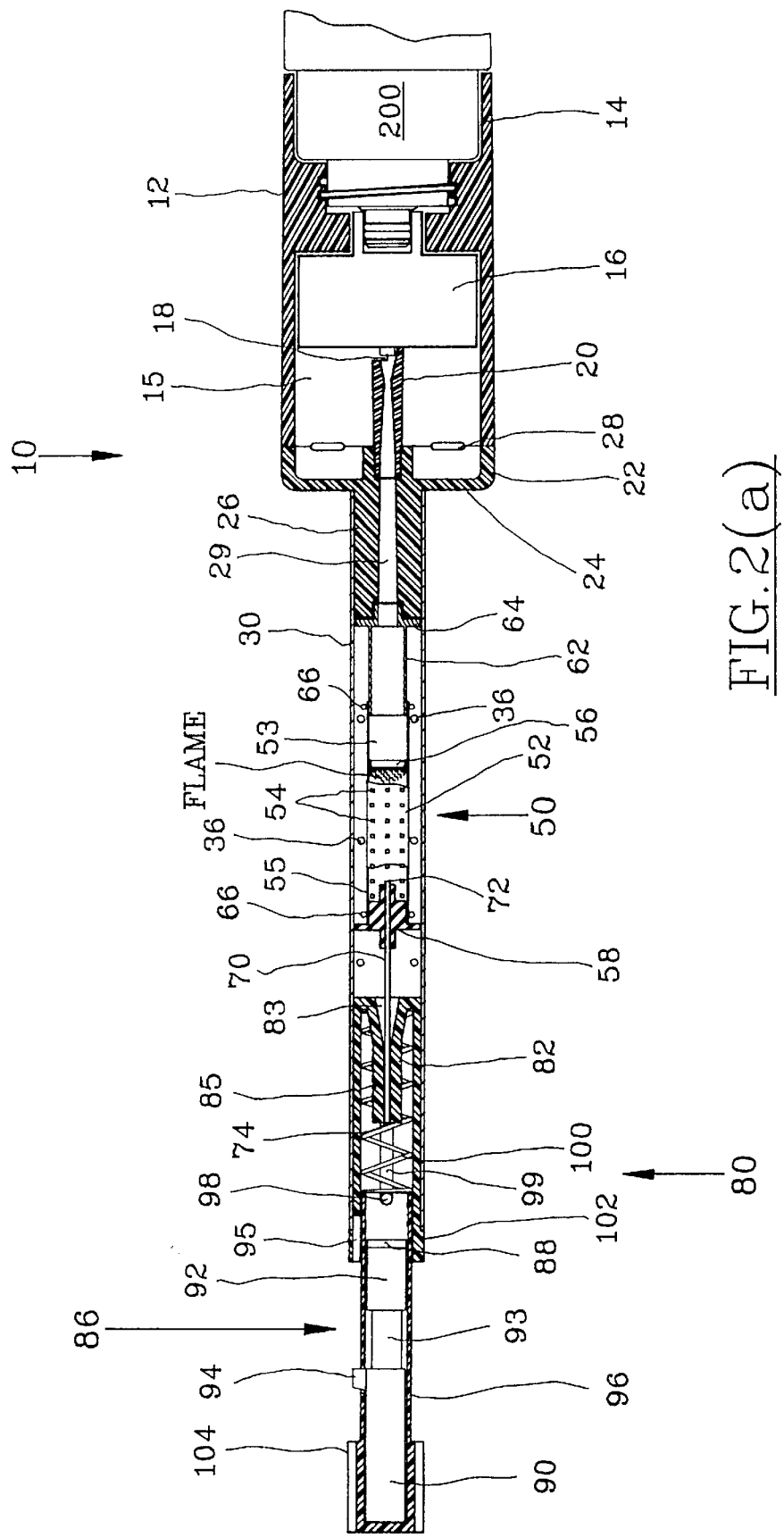
FIG. 2(a) is a partial section view of the curling iron of FIG. 1 taken along the line II—II in FIG. 1, showing a portion of the catalytic assembly broken away and the piezoelectric ignitor fully extended from the barrel.

The present invention eliminates the above-mentioned disadvantages of conventional devices. The catalytic substrate is a perforated metal or wire screen structure that will allow gases to pass freely through it. Preferably, the metal cylinder is perforated over only one portion, thereby forming perforated and non-perforated areas. The substrate is preferably closed such that it has no openings larger than one of the perforations or screen pores, and one end of the ignition spark electrode is located inside this enclosure. The perforated metal will not allow flame to pass through itself, so the catalytic heater is self-flame-arresting, requiring no other explosion protection. The catalytic structure is preferably cylindrical, with the perforated and catalyzed metal forming the periphery of the cylinder. One end of the cylinder is closed with a solid piece of material which contains an ignition electrode and an insulator to electrically insulate the electrode from the substrate. The other end of the cylinder is closed with a wire mesh screen or alternatively perforated metal. A fuel/air mixture is introduced through the screened end of the cylinder. The size of the screen is adjusted to the flow rate of fuel and air such that a sustained flame will initially burn on the burner screen inside the substrate. Preferably, the burner screen is located at a point in the catalyst structure between perforated and non-perforated portions.

When a voltage is applied between the electrode and the substrate in a manner to be explained below, a spark jumps between the electrode and the nearest point on the substrate. Assuming the fuel/air mixture is correct, the spark ignites a blue flame which burns on the screen. If no catalytic material were present, the flame would burn in a continuous and sustained manner, as fresh fuel and primary intake air are introduced through the screen, exhaust products leave through the perforated substrate, and external or secondary combustion air enters through the substrate. By introducing the catalytic material (platinum, palladium, etc.), some of the fuel air mixture in the area of the flame will combust catalytically, and the exhaust products of this catalytic reaction will poison and extinguish the flame. The catalytic reaction then spreads over the catalytic substrate such that all of the fuel/air mix will be combusted on the catalyst. In actual operation, it may take a few seconds from the time of the spark until the catalytic reaction has extinguished the flame and spread over the substrate.

The advantages to this construction are numerous. First, all ignition and combustion occur inside the catalyst structure; there is thus no need, from a fire or explosion safety stand-point, to place a flame arresting enclosure around the catalyst. Second, the perforated metal substrate can be of a substantially heavier and stronger gauge material than that of the Schaefer et al. patent, because the sustained blue flame has enough energy to raise the substrate temperature to the point of catalytic reaction; multiple explosions are not necessary. Third, the catalytic material can have a much lower activity (e.g., less surface area, lower amount of precious metal, lower-cost metals such as palladium instead of platinum) and will still function because of the use of a sustained ignition source instead of an explosion. Should the catalyst lose some activity, ignition time will only slightly be increased. Moreover, the overall dimensions of the structure are smaller than those of conventional devices, resulting in fewer materials required for manufacture and thus lower costs to the consumer.

A description will now be given with reference to the figures as exemplifying the invention. The embodiment illustrated is for a portable gas-powered hair curling iron; however, the applications of the invention are numerous and varied, and it is not limited to curling irons or hair care appliances.

As shown in the figures, appliance 10 includes housing 12 which contains the fuel flow path from to-be-attached fuel cartridge 200. Fuel cartridge 200 typically contains a gaseous or liquid fuel such as butane or propane, and fits into recess 14 of housing 12. Threads may be provided in recess 14 to mate with threads on cartridge 200 to lock the cartridge in place. Alternatively, instead of receiving a pre-filled fuel cartridge, housing 12 may be provided with a fillable fuel chamber (not shown) into which fuel would be added. Housing 12 is substantially hollow and has main cavity 15 in which the majority of the fuel flow path is disposed.

Inside cavity 15 in communication with recess 14 is flow control device 16, which in this example is a single stage pressure regulator. Flow control device 16 regulates the flow of fuel from fuel cartridge 200 to the rest of the appliance. In some cases, the mere attachment of fuel cartridge 200 initiates the flow of fuel from the cartridge through flow control device 16. In other cases, a valve (not shown) may be opened manually by the user. In either event, when fuel pressure has built up to a certain level, fuel passes through flow control device 16 and exits from a small opening in gas jet 18. The opening in gas jet 18 is preferably 35–40 micrometers (0.00138–0.00157 inches) in diameter. Gas jet 18 is in communication with the entrance of venturi tube 20, however it is not sealingly engaged with venturi tube 20. That is, the entrance of venturi tube 20 is open and exposed to cavity 15 of housing 12, so that when fuel from gas jet 18 enters the venturi tube, air is entrained along with the fuel to produce a fuel/air mixture that enters venturi tube 20.

Housing 12 is attached to barrel holder 22, which is provided to support barrel 30 as described below. Barrel holder 22 includes housing attachment portion 24, which fits onto housing 12. Attachment portion 24 may be secured to housing 12 in any number of ways, including press-fitting, screws, snapping on with mating tabs, sonic welding, or the like. Notches are formed in one or both of housing 12 and attachment portion 24, so that when the two pieces are fitted together, primary air vents 28 are formed. Air vents 28 allow main cavity 15 of housing 12 to communicate with ambient air, and allow air to enter cavity 15 and mix with fuel from gas jet 18.

Barrel holder 22 also possesses projection 26 extending from attachment portion 24. Barrel 30 fits around projection 26 and is supported therefrom in a cantilever manner. Projection 26 includes a central passageway 29 that allows the fuel/air mixture exiting from venturi tube 20 to travel to the rest of the appliance for combustion purposes.

Barrel 30 includes the main surface through which heat is transferred from the combustion of the fuel/air mixture to the hair being wound around it. It should therefore be a good conductor of heat, and for reasons explained below, it should also be a good electrical conductor. Secondary air vents 36 are provided in barrel 30 to allow ambient air to communicate with the interior of the barrel, and to allow the products of combustion of the fuel/air mixture to escape from the interior of the barrel.

Catalytic assembly 50, responsible for the Blameless combustion of the fuel, is disposed in barrel 30. The assembly is in communication with passageway 29 of projection 26, so that the fuel/air mixture exiting from venturi tube 20 is fed through to the interior of the assembly via mounting tube 62. Mounting tube 62 is electrically conductive for reasons which shall become clear below and has a conductive flange 64 contacting barrel 30. That is, barrel 30 and catalytic assembly 50 are electrically connected via conductive flange 64 of mounting tube 62, and are at the same potential.

Figure 2B:
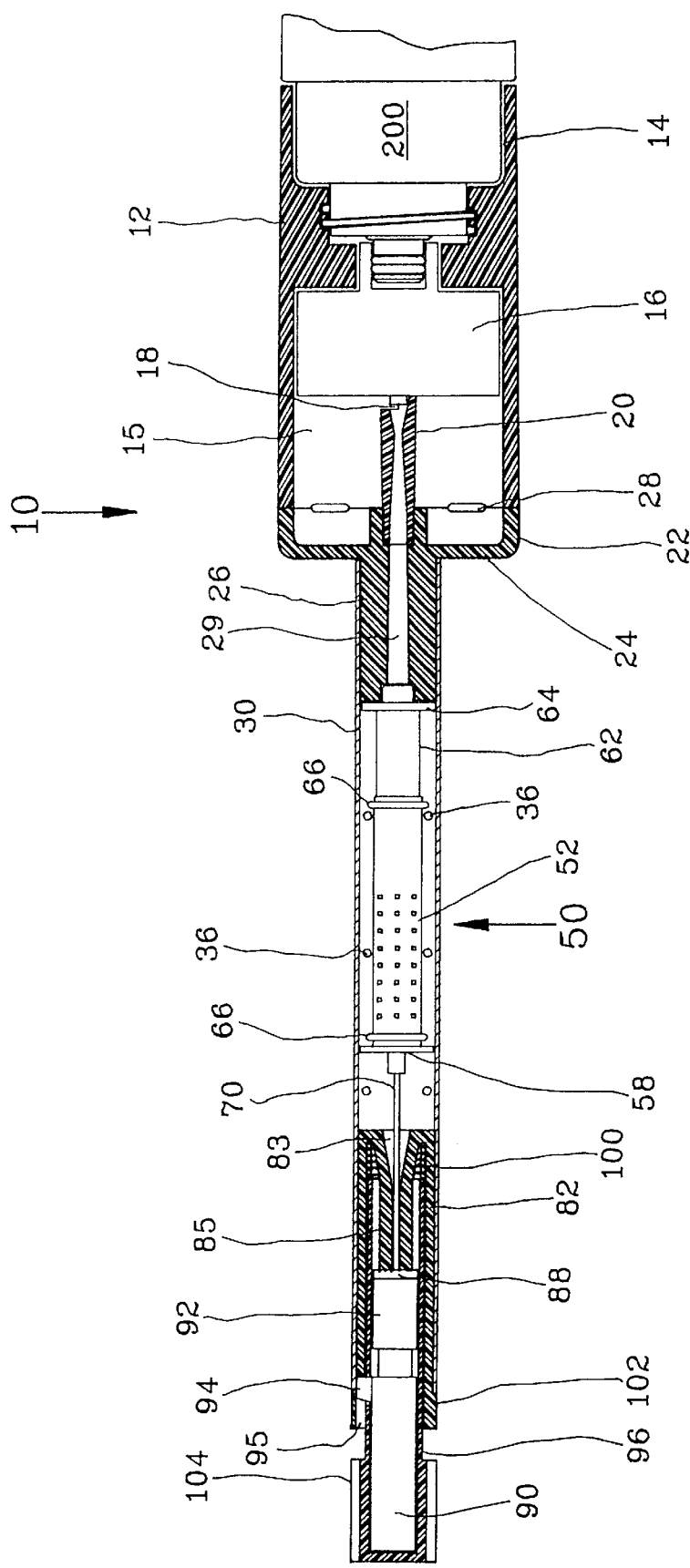
FIG. 2(b) is a partial section view of the curling iron of FIG. 1 taken along the line II—II in FIG. 1, showing the piezoelectric ignitor fully depressed into the barrel.
Figure 3:
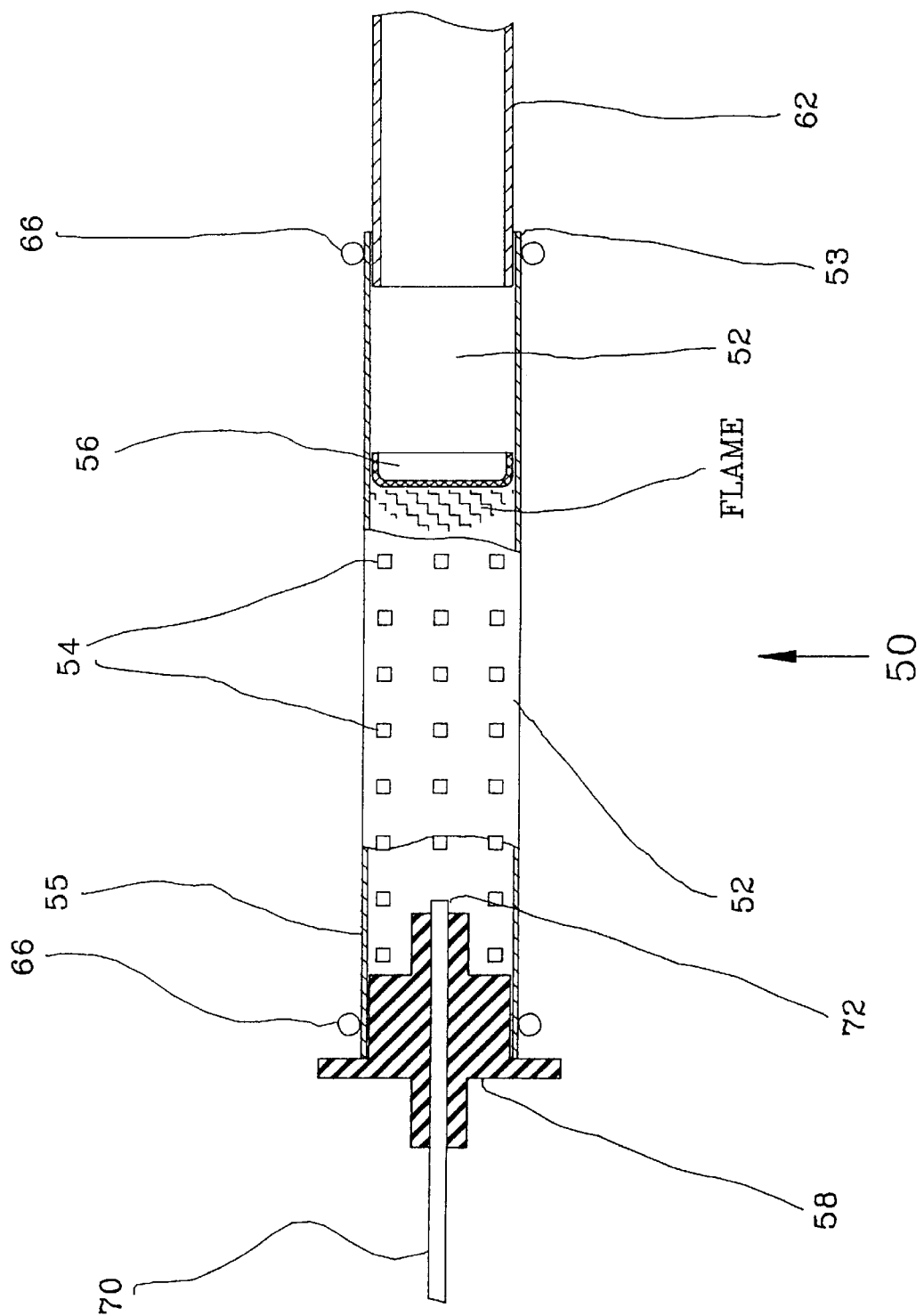
FIG. 3 is a partially broken section view of the catalyst assembly shown in FIG. 2(a).

The catalyst assembly 50 includes catalytic support 52, a metallic preferably tubular substrate on which a catalytic material such as palladium is disposed on at least an inner surface. First end 53 of support 52 is in communication with mounting tube 62 so as to allow the fuel/air mixture to proceed to the combustion zone of the device. Retaining rings 66 are used to secure catalytic support 52 to mounting tube 62 and plug 58 (described below) to support 52. Perforations 54 are made in catalytic support 52 which allow the products of combustion formed inside support 52 to escape. However, the perforations are small enough to prevent flames from exiting the support. As illustrated in FIGS. 2(a)–(b), perforations 54 are only provided on a portion of support 52. At or near the point where perforations 54 end is disposed a burner nozzle preferably in the form of a wire mesh burner screen 56 on the interior of structure 52 (see FIG. 2(a)). The burner nozzle reduces the cross-sectional area of structure 52 and halts the propagation of a flame front moving towards first end 53. During the first few seconds after ignition of the fuel, the flame produced inside support 52 will thus form on burner screen 56. The other end 55 of catalytic support 52 includes electrically insulative plug 58, through which is disposed spark electrode 70. Spark electrode 70 has a first end 72 which extends into the interior of catalytic support 52. A voltage potential can be created between electrode 70 and support 52, as described below.

Catalytic support 52 is preferably formed from stainless steel sheet approximately seven thousandths (0.007) of an inch thick. The sheet metal is perforated over approximately three fourths of its area. Perforations 54 are 1/32 of an inch square in size, or 1/32 of an inch in diameter if round, and spaced 0.080 inches apart both longitudinally and circumferentially. The perforated metal is then formed into a cylinder approximately ¼ inch in diameter and 1¼ inches long. At this stage the substrate may be treated with a catalytic coating. A disc of stainless steel screen, about ¼ inch in diameter, is attached inside the cylinder at the location between the perforated and non-perforated portions of the cylinder to serve as burner screen 56. The burner screen mesh size is preferably 40 wires per inch, and the wire diameter is preferably 13 thousandths (0.013) of an inch. Insulator plug 58 is preferably made of molded ceramic. For the described geometry, a butane flow rate of 0.5 to 2.0 grams per hour, mixed with air in the ratio of approximately 30 volumes air to one volume butane vapor, will produce a sustained internal flame for ignition and will be subsequently completely combusted catalytically as it passes through catalytic support 52.

When the voltage potential is created and the fuel/air mixture is present inside catalytic support 52, a spark between catalytic support 52 and electrode 70 ignites the fuel/air mixture, and causes a flame front to propagate. Under proper flow conditions, the flame front travels in the opposite direction of the flow of the fuel/air mixture (i.e., from left to right in FIG. 2(a)), until the flame front settles on burner screen 56. The flame heats the catalytic material disposed on the interior of support 52, and catalytic combustion begins.

The ignition assembly 80 creates the voltage potential between spark electrode 70 and catalytic support 52. Spark electrode 70 is supported in protuberance 85 of non-conductive mounting plug 82, which has a bore 83 formed therethrough. End 74 of spark electrode 70 (i.e., the end not disposed inside catalytic support 52) is electrically accessible through the terminus of bore 83. In other words, end 74 is either flush with or only slightly recessed inside the terminus of bore 83, thereby allowing a charge to be placed on electrode 70 via end 74.

Figure 4:
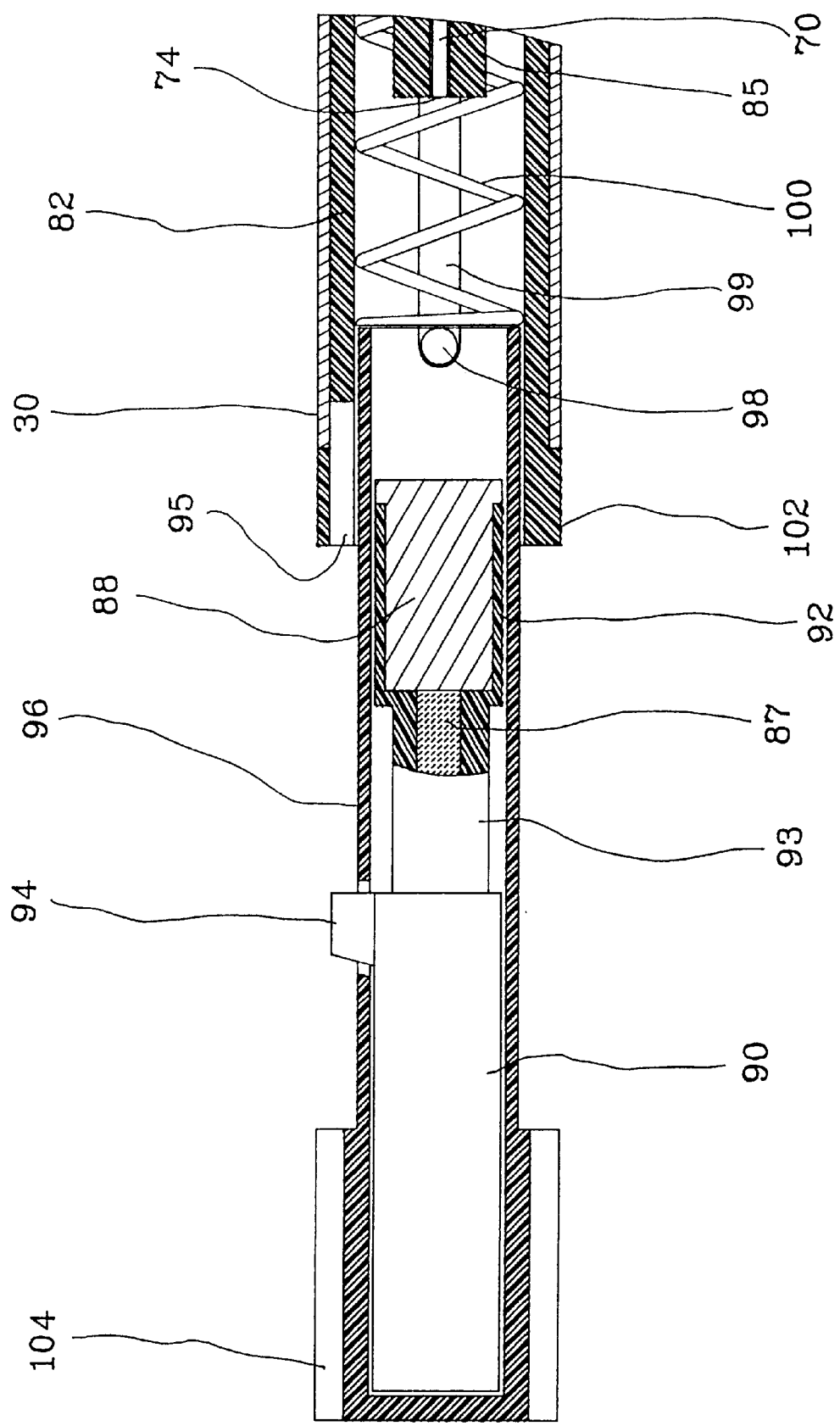
FIG. 4 is partially broken section view of the piezoelectric ignitor shown in FIGS. 2(a) and 2(b).

A piezoelectric device 86 is provided at the very end of barrel 30 to create the voltage potential between spark electrode 70 and catalytic support 52. It includes a piezoelectric element or crystal 87 (see FIG. 4) which, when compressed along a certain axis, creates a voltage potential across itself. First conductive piece 88 can contact one side of piezoelectric element 87 and second conductive piece 90 can contact the other side of piezoelectric 87. The piezoelectric element is carried by non-conductive carrier piece 92 upon which first conductive piece 88 is mounted. Carrier piece 92 has a necked-down portion 93 that allows carrier piece 92 to telescope inside second conductive piece 90. A biasing spring (not shown) keeps carrier piece 92 and second conductive piece 90 apart as shown in FIG. 2(a). When the two conductive pieces are squeezed together, piezoelectric element 87 inside carrier piece 92 is compressed in a known manner, and a voltage potential is created across the element. Since the two conductive pieces 88 and 90 are in contact with the two ends of piezoelectric element 87, respectively, the two conductive pieces have the same voltage potential as the two ends of the element when the potential is created.

Second conductive piece 90 has conductive projection 94 which will contact barrel 30 when second conductive piece 90 is pushed inside barrel 30. Conductive projection 94 slides along channel 95 formed in mounting plug 82 when piezoelectric device 86 is slid inside barrel 30. Thus, barrel 30 will be at the same potential as second conductive piece 30. Moreover, when second conductive piece 90 is pushed inside barrel 30, first conductive piece 88 is pressed against protuberance 85 of mounting plug 82 and is in electrical contact with end 74 of spark electrode 70. Thus, spark electrode 70 will be at the same potential as first conductive piece 88.

Piezoelectric device 86 is encapsulated by an insulative cover 96 which has stop pins 98 provided at one end. Stop pins 98 are disposed in grooves 99 formed in mounting plug 82; the ends of grooves 99 engage stop pins 98 when the piezoelectric device is pushed to its farthest point out of the barrel, thereby preventing piezoelectric device 86 from falling out of barrel 30. Biasing spring 100 is provided to push against the end of insulating cover 96 and forces the piezoelectric device in a direction out of barrel 30. Collar 102 of mounting plug 82 is provided in the very end of barrel 30 to maintain proper spacing between the piezoelectric device and the hot barrel 30 when the appliance is in use. Collar 102 also helps to prevent burns in the case where a user depresses the piezoelectric device completely inside barrel 30 when the barrel is already hot. A gripping member or cap 104 is disposed on the very end of insulating cover 96 to facilitate a user of the appliance in depressing ignition assembly 80 into barrel 30 and causing the spark to form between catalytic support 52 and spark electrode 70. The gripping member is preferably non-conductive of both electricity and heat, to prevent the user from electric shock and burns from the hot barrel.

The operation of the appliance is as follows, with reference being given primarily to FIGS. 2(a) and (b). A butane cartridge 200 is attached with a gas-tight O-ring seal to the flow control device 16, which in this embodiment is a single-stage pressure regulator. This action initiates the flow of fuel, and the gas pressure in the regulator quickly rises to the preset pressure, which is preferably in the range of 5–10 psig. The butane vapor exits through gas jet 18 and enters a venturi tube 20 into which air is entrained through the primary air intake vents 28 into cavity 15. The size of the gas jet (preferably 30–40 micrometers), the venturi throat diameter (preferably 0.03–0.05 inches), and the regulator pressure are selected to provide an air-to-fuel mixture ratio of approximately 30 volume air to one volume butane. The fuel/air mixture passes through mounting tube 62 and into the catalyst assembly.

The piezoelectric device 86 shown in the figures is manufactured by Feudor S.A. and is a low-cost type used in disposable cigarette lighters. Second conductive piece 90 is made of electrically conductive plastic, and first conductive piece 88 is a metal cap. As explained above, the voltage potential generated by the device 86 occurs across these two elements 88 and 90. The device is biased away from the heater by coil spring 100. FIG. 2(a) shows the normal biased position of the assembly. It is desirable to minimize the exposure of the piezoelectric device to excessive heat, and this arrangement serves to distance the device from the heat source during extended operation, as does the provision of collar 102 of mounting plug 82. To ignite the curling iron, the user depresses gripping member 104. FIG. 2(b) shows the fully depressed position, which causes piezoelectric device 86 to fire. Metal cap 88 is brought into contact with end 74 of electrode 70 (at the end face of protuberance 85), and the projection 94 from the conductive plastic portion 90 is brought into contact with metal barrel 30. Barrel 30 is in contact with mounting tube 62, which is made of metal and is in contact with the catalytic support 52 which is also metallic. A high voltage potential (approximately 10,000 volts) is generated between electrode 70 and the surrounding metal parts, and a spark jumps across the smallest available gap, which is between end 72 of electrode 70 and the nearest point on the support 52. Since the fuel/air flow is already established within the support 52, the spark initiates a flame front, which propagates against the flow until it reaches burner screen 56 which stabilizes the position of the flame as shown in FIG. 2(a). The size of the flame is small compared to the support, approximately 1/8 inch long. As a result the small portion of support 52 nearest screen 56 temporarily receives most of the heat released by the hot (approximately 1,700° C.), blue, stoichiometric flame. After a short time (1 or 2 seconds), the non-perforated portion of the support receives enough heat by conduction to reach the temperature at which catalytic combustion occurs. As soon as any catalytic activity occurs upstream of the flame, the exhaust products ($CO_2$, $H_2O$, and excess $N_2$) quickly poison the flame and cause it to extinguish. The catalytic reaction is then able to spread over the remainder of the perforated portion of the catalyst, with this reaction taking place at a much lower temperature (400–500° C.) than the flame temperature. This lower temperature allows for a long service life of the catalyst.

Secondary air for combustion enters and exhaust products are carried away through secondary air vents 36 in barrel 30. As long as the fuel flow is on and constant, the catalytic reaction will continue at a constant rate, and barrel 30 will be heated and maintained at a desirable equilibrium temperature e.g., 140–180° C. for a curling iron. The operation is stopped when the user removes the butane cartridge 200 or when the cartridge runs out of fuel. An on/off switch may be included in the pressure regulator if desired.

The flame-arresting benefit of this catalyst construction works in two ways, characterized as "inside-out" and "outside-in."

Inside-out: The ignition spark and the temporarily sustained flame are contained within the catalyst support structure, which is formed from a thermally conductive metal through which a flame cannot propagate without being quenched. During the catalytic combustion process, the temperature of the cylinder (400–500° C.) is too low to serve as an ignition source. Thus, this heater construction will not ignite external flammable vapors (for example, hair spray) in its vicinity.

Outside-In: When the fuel flow is on but without having been ignited from inside, the fuel/air mixture is distributed through the relatively large perforated area of the catalyst. The velocity of the flow leaving the catalyst is very low, and a flame will not be sustained on the outside of the catalyst. The device is therefore impossible to ignite using an external ignition source.

Other advantages of the present invention include reduction in size and therefore manufacturing costs. The device shown in the figures is a cordless hair curling iron. The Schawbel Corporation currently manufactures a line of cordless curling irons as described- in U.S. Pat. No. 4,699, 123 and additional patents. The curling irons have barrels ranging in size from 5/8 to 1½ inches in diameter. The 5/8 inch size was found to be the practical lower size limit due to constraints of burner and ignition electrode arrangements required. Braun, Inc. manufactures a line of catalytic gas curling irons as described in the Schaefer et al. patent. The barrel sizes range from approximately 11/16 inch to 1 1/8 inch diameter. Their system relies on the energy released by exploding the volume of gas mixture within the barrel and outside the catalyst in order to ignite the catalyst. Additionally, the ignition electrode is placed between the outside of the catalyst and the inside of the barrel; maintaining a proper spark gap thus puts a lower limit on the barrel size. Conventional electric curling irons are made with very small diameter barrels, sometimes only ¼ inch, for making very tight curls. The present invention, as shown in the figures will easily fit and function within a barrel only 3/8 inch in diameter.

Another benefit compared with the previous technology is found in very low heat applications. There are a number of electrical products whose power is in the range of 5–10 watts, for example, heated air freshener devices. A 1.25 gram per hour butane flow rate has been found to be a practical minimum for sustaining an enclosed flame for extended periods of time. This corresponds to a power of 17 watts. With smaller flow rates, the flame tends to be extinguished after some period of operation, especially if disturbed by air movement. If it were desired to have a low heat (0.5–1.25 grams butane per hour), extended use (a small 12 gram butane refill will last from 9.6 to 24 hours at these flow rates), cordless heated appliance, the present invention would be well suited to this application.

Finally, the present invention is beneficial to use in all the current applications (standard size and larger curling irons, soldering irons, glue guns, etc.) because of its simple construction, reliability of ignition, and inherent ability to remain lit once ignited.

Having described the invention with regard to specific embodiments, it is to be understood that the description is not meant as a limitation excluding such further variations or modifications as may be apparent or may suggest themselves to those skilled in the art. It is intended that the present invention cover such variations and modifications as fall within the scope of the appended claims. For example, the above description makes reference to a burner screen in the catalytic assembly provided to stabilize the flame front. However, other structures that arrest flame propagation would also be suitable, such as a spline gear or an annular disc. In another example, a spark electrode is described as the ignition source for the fuel. However, a hot wire could serve as the ignition source as well.

What is claimed is:

1. A catalytic combustion assembly for a portable heating appliance, comprising:
   an enclosed at least partially perforated structure having first and second ends and an interior volume and at least one perforation;
   an opening at said first end in communication with said interior volume and adapted to receive a combustible fuel mixture;
   an ignition source mounted on one of said first and second ends extending into said interior volume of said structure;
   flame retention means for supporting a flame for heating said structure to a catalytic temperature, said means disposed in said interior volume of said structure; and
   catalytically active material provided on at least an internal surface of said structure.

2. A catalytic combustion assembly according to claim 1, wherein said at least one perforation comprises a plurality of perforations in said structure, said perforations allowing said interior volume to communicate with an environment outside of said structure.

3. A catalytic combustion assembly according to claim 2, wherein said perforations are provided on only a portion of said structure.

4. A catalytic combustion assembly according to claim 2, wherein said perforations are provided on only one longitudinal portion of said structure, thereby forming a perforated longitudinal section and a non-perforated longitudinal section.

5. A catalytic combustion assembly according to claim 4, wherein said burner nozzle is provided substantially at a point between said perforated longitudinal section and said non-perforated longitudinal section.

6. A catalytic combustion assembly according to claim 1, wherein said ignition source is mounted on said second end of said structure.

7. A catalytic combustion assembly according to claim 1, further comprising an electrical insulator disposed in said second end of said structure, wherein said ignition source is mounted in said insulator on said second end of said structure.

8. A catalytic combustion assembly according to claim 1, wherein said burner nozzle is provided substantially perpendicular to a longitudinal axis of said structure.

9. A catalytic combustion assembly according to claim 1, wherein said burner nozzle is provided between said ignition source and said opening.

10. A catalytic combustion assembly according to claim 1, wherein said catalytically active material is adapted to enable flameless combustion of fuel on said surface of said structure.

11. A catalytic combustion assembly according to claim 1, wherein said structure is a hollow metal tube.

12. A catalytic combustion assembly according to claim 1, wherein said flame retention means comprises a wire mesh.

13. A catalytic combustion assembly according to claim 1, wherein said ignition source comprises a spark electrode.

14. A portable heating appliance comprising:
    a housing, said housing containing a flow path for a combustible fuel mixture; and
    a catalytic combustion assembly, disposed in communication with said flow path, wherein said catalytic combustion assembly comprises
       an enclosed at least partially perforated structure having first and second ends and an interior volume and at least one perforation;
       an opening at said first end of said structure adapted to receive the combustible fuel mixture exiting from said flow path;
       an ignition source mounted on one of said first and second ends of said structure extending into said interior volume of said structure;
       flame retention means for supporting a flame for heating said structure to a catalytic temperature, said means disposed in said interior volume of said structure; and
       catalytically active material provided on at least an internal surface of said structure.

15. A portable heating appliance according to claim 14, further comprising a barrel projecting from said housing, wherein said catalytic combustion assembly is disposed in an interior of said barrel.

16. A portable heating appliance according to claim 15, said housing further comprising a projection extending from one end of said housing, wherein said barrel is supported by said projection.

17. A portable heating appliance according to claim 15, further comprising second air vents formed in said barrel allowing communication between ambient air outside said barrel and air inside said barrel.

18. A portable heating appliance according to claim 15, further comprising an electrical insulator disposed in said second end of said structure, wherein said ignition source is mounted in said electrical insulator on said second end of said structure.

19. A portable heating appliance according to claim 15, wherein said ignition source comprises a spark electrode having a first end and a second end, wherein said first end of said spark electrode terminates in the interior of said structure, said appliance further comprising a non-conductive mounting plug disposed in said interior volume of said barrel, wherein said second end of said spark electrode is disposed in said mounting plug so that said second end of said spark electrode is exposed at an end of an inner portion of said mounting plug.

20. A portable heating appliance according to claim 19, further comprising a piezoelectric device, slidably disposed in an end of said barrel and electrically connectable to said spark electrode and said barrel, adapted to create a voltage potential between said spark electrode and said barrel.

21. A portable heating appliance according to claim 20, further comprising a biasing spring disposed inside said barrel, adapted to bias against said piezoelectric device and tending to push said piezoelectric device in a direction out of said end of said barrel.

22. A portable heating appliance according to claim 21, further comprising:
   a collar mounted in said end of said barrel; and
   an insulative cover, substantially surrounding said piezoelectric device and adapted to prevent said biasing spring from pushing said piezoelectric device completely out of said barrel.

23. A portable heating appliance according to claim 22, wherein said insulative cover comprises an aperture for allowing electrical contact between said piezoelectric device and said barrel.

24. A portable heating appliance according to claim 23, further comprising a conductive projection formed on said piezoelectric device and extending through said aperture of said insulative cover, adapted to electrically contact said barrel when said projection is slid inside said barrel.

25. A portable heating appliance according to claim 19, further comprising a conductive retaining piece, disposed in said barrel fixedly securing said catalytic combustion assembly inside said barrel and electrically connecting said structure of said catalytic combustion assembly to said barrel.

26. A portable heating appliance according to claim 25, further comprising a piezoelectric device, slidably disposed in an end of said barrel and electrically connectable to said spark electrode and said barrel, adapted to create a voltage potential between said spark electrode and said structure of said catalytic combustion assembly.

27. A portable heating appliance according to claim 26, wherein said piezoelectric device is reciprocatably slidable into and out of said end of said barrel and comprises:
   a first conductive portion adapted to be electrically connectable to said second end of said spark electrode;
   a non-conductive carrier piece on which said first conductive portion is mounted;
   a piezoelectric element having first and second ends, disposed inside said non-conductive carrier piece, adapted to create said voltage potential between said first and second ends of said piezoelectric element; and
   a second conductive portion in telescoping arrangement with said first conductive portion, said second conductive portion adapted to be electrically connectable to said barrel when said second conductive portion is slid inside said barrel,
   wherein said first conductive portion is electrically connectable with said first end of said piezoelectric element and said second conductive portion is electrically connectable with said second end of said piezoelectric element.

28. A portable heating appliance according to claim 27, further comprising a biasing spring disposed inside said barrel, adapted to bias against said piezoelectric device and tending to push said piezoelectric device in a direction out of said end of said barrel.

29. A portable heating appliance according to claim 28, further comprising:

a collar mounted in said end of said barrel; and
an insulative cover, substantially surrounding said piezoelectric device and adapted to prevent said biasing spring from pushing said piezoelectric device completely out of said barrel.

30. A portable heating appliance according to claim 29, wherein said insulative cover comprises:
   a first end;
   a second end into which said second conductive portion of said piezoelectric device is disposed; and
   an aperture for allowing electrical contact between said second conductive portion and said barrel.

31. A portable heating appliance according to claim 30, further comprising a conductive projection disposed on said second conductive portion of said piezoelectric device and extending through said aperture of said insulative cover, adapted to electrically contact said barrel when said second conductive portion is slid inside said barrel.

32. A portable heating appliance according to claim 30, said insulative cover further comprising a cap disposed on said first end of said insulative cover and adapted to facilitate depression of said piezoelectric device into said barrel.

33. A portable heating appliance according to claim 30, said insulative cover further comprising stop pins disposed at said second end of said insulative cover and adapted to prevent movement of said piezoelectric device out of said end of said barrel beyond a predetermined point.

34. A portable heating appliance according to claim 14, further comprising first air vents formed in said housing allowing communication between ambient air outside said housing and air and fuel inside said housing.

35. A portable heating appliance according to claim 14, wherein said flame retention means comprises a wire mesh.

36. A portable heating appliance comprising:
   a housing, said housing containing a flow path for a combustible fuel mixture;
   a barrel projecting from said housing, an interior of said barrel being in communication with said flow path, said barrel having a free end;
   a catalytic combustion assembly disposed in said interior of said barrel having: an enclosed at least partially perforated structure having first and second ends, an interior volume, and at least one perforation; an opening at said first end in communication with said interior volume and adapted to receive the combustible fuel mixture; flame retention means for supporting a flame for heating said structure to a catalytic temperature, said means disposed in said interior volume of said structure; and catalytically active material provided on at least an internal surface of said structure; and
   a piezoelectric ignitor disposed in said free end of said barrel adapted to ignite the fuel mixture inside said barrel, said piezoelectric ignitor further comprising a spark electrode having first and second ends disposed in said barrel, and a non-conductive mounting plug disposed in the interior of said barrel, wherein said second end of said spark electrode is disposed in said mounting plug so that said second end of said spark electrode is exposed at an end of an interior portion of said mounting plug and extends into said interior volume of said structure.

37. A portable heating appliance according to claim 36, said piezoelectric ignitor further comprising a piezoelectric device, slidably disposed in said free end of said barrel and electrically connectable to said spark electrode and said barrel, adapted to create a voltage potential between said spark electrode and said barrel.

38. A portable heating appliance according to claim 37, wherein said piezoelectric device is reciprocatably slidable into and out of said end of said barrel and comprises:

- a first conductive portion adapted to be electrically connectable to said second end of said spark electrode;
- a non-conductive carrier piece on which said first conductive portion is mounted;
- a piezoelectric element having first and second ends, disposed inside said non-conductive carrier piece, adapted to create said voltage potential between said first and second ends of said piezoelectric element; and
- a second conductive portion in telescoping arrangement with said first conductive portion, said second conductive portion adapted to be electrically connectable with said barrel when said second conductive portion is slid inside said barrel,
- wherein said first conductive portion is electrically connectable with said first end of said piezoelectric element and said second conductive portion is electrically connectable with said second end of said piezoelectric element.

39. A portable heating appliance according to claim 38, said piezo electric ignitor further comprising a biasing spring, adapted to bias against said piezoelectric device and tending to push said piezoelectric device in a direction out of said end of said barrel.

40. A portable heating appliance according to claim 39, said piezoelectric ignitor further comprising:

- a bushing, mounted in said end of said barrel; and
- an insulative cover, substantially surrounding said piezoelectric device and adapted to abut said bushing to prevent said biasing spring from pushing said piezoelectric device completely out of said barrel.

41. A portable heating appliance according to claim 40, wherein said insulative cover comprises:

- a first end;
- a second end into which said second conductive portion of said piezoelectric device is disposed; and
- an aperture for allowing electrical contact between said second conductive portion and said barrel.

42. A portable heating appliance according to claim 41, said piezoelectric ignitor further comprising a conductive projection disposed on said second conductive portion of said piezoelectric device and extending through said aperture of said insulative cover, adapted to electrically contact said barrel when said second conductive portion is slid inside said barrel.

43. A portable heating appliance according to claim 41, said insulative cover further comprising stop pins disposed at said second end of said insulative cover and adapted to prevent movement of said piezoelectric device out of said end of said barrel beyond a predetermined point.

44. A portable heating appliance according to claim 41, said insulative cover further comprising a cap disposed on said first end of said insulative cover and adapted to facilitate depression of said piezoelectric device into said barrel.

* * * * *